United States Patent
Bhaskar et al.

(10) Patent No.: US 7,379,838 B2
(45) Date of Patent: May 27, 2008

(54) PROGRAMMABLE IMAGE COMPUTER

(75) Inventors: Krishnamurthy Bhaskar, San Jose, CA (US); Mark J. Roulo, Mountain View, CA (US); John S. Taylor, San Jose, CA (US); Lawrence R. Miller, Los Altos, CA (US); Paul T. Russell, Scotts Valley, CA (US); Jason Z. Lin, Saratoga, CA (US); Eliezer Rosengaus, Palo Alto, CA (US); Richard M. Wallingford, San Jose, CA (US); Kishore Bubna, Fremont, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 11/530,153

(22) Filed: Sep. 8, 2006

(65) Prior Publication Data

US 2007/0005284 A1 Jan. 4, 2007

Related U.S. Application Data

(62) Division of application No. 10/967,388, filed on Oct. 18, 2004, now Pat. No. 7,149,642.

(51) Int. Cl.
*G06F 15/00* (2006.01)

(52) U.S. Cl. .................................. 702/127; 382/145

(58) Field of Classification Search ............. 702/40, 702/127, 116, 122, 186; 382/141, 144, 145, 382/149; 358/1.13, 1.15
See application file for complete search history.

(56) References Cited

U.S. PATENT DOCUMENTS

| 6,509,978 | B1 * | 1/2003 | Szumla ................... 358/1.8 |
| 6,707,463 | B1 * | 3/2004 | Gibson et al. ............. 345/619 |
| 6,862,101 | B1 * | 3/2005 | Miyazaki et al. .......... 358/1.13 |
| 7,072,058 | B1 * | 7/2006 | Miyazaki et al. .......... 358/1.15 |
| 7,181,368 | B1 * | 2/2007 | Bhaskar et al. ........... 702/185 |

* cited by examiner

*Primary Examiner*—Bryan Bui
(74) *Attorney, Agent, or Firm*—Luedeka, Neely & Graham, P.C.

(57) ABSTRACT

An inspection system for detecting anomalies on a substrate. A first network is coupled to a sensor array and communicates data. Process nodes are coupled to the first network, and process the data to produce reports. Each process node has an interface card that formats the data for a high speed interface bus that is coupled to the interface card. A computer receives and processes the data to produce the report. A second network receives the reports. A job manager is coupled to the second network, receives the reports, and sends information to the process nodes to coordinate processing of the data.

1 Claim, 2 Drawing Sheets

PROGRAMMABLE IMAGE COMPUTER

This invention relates to the field of integrated circuit fabrication. More particularly, this invention relates to substrate inspection systems. This application relates to the copending applications listed below, all of which were filed on Oct. 18, 2004:

| Application Ser. No. | U.S. Pat. No. |
|---|---|
| 10/967,397 | 7076390 |
| 10/967,419 | 7181368 |
| 10/967,542 | |
| 10/967,375 | |
| 10/967,838 | 7024339 |
| 10/967,500 | |
| 10/967,376 | |
| 10/967,832 | |
| 10/967,420 | |
| 10/967,418 | |

BACKGROUND

Integrated circuit manufacturers use inspection systems to detect anomalies, such as defects, in substrates. Generally, an inspection system rasters the surface of the substrate with one or more optical sensors, and generates image data based on the images detected by the sensors. This image data is analyzed according to one or more of a variety of different algorithms to determine where defects might exist on the substrate. Integrated circuit manufacturers demand that such inspection systems meet several criteria. Among these criteria is that the inspection system must be extremely accurate, fast, and reliable. Further, such inspection systems should preferably be reasonably priced and relatively flexible.

Prior art inspection systems have implemented one or both of pipelined systems or computers that are networked in a switched fabric topology, which use highly customized hardware. Customized hardware has several disadvantages as compared to commercially available hardware, including higher nonrecurring engineering costs for the developer, lower reliability, longer development times, and more inflexibility in changing algorithms. Switched fabric systems have additional disadvantages, including high cost, lack of standards between manufacturers, and development lag in the components, such as the level of microprocessor that is built into such systems.

Commercial hardware, by contrast, tends to be more reliable, more versatile, and less expensive. For example, large computer manufacturers devote a tremendous amount of engineering effort to ensure that the latest technologies are implemented in their products, and that those products are brought to market as soon as possible. This large engineering effort is then factored into the price of the many, many units that they anticipate selling. Thus, the large development costs are spread quite thin as to each unit that is purchased. The development costs for customized hardware, on the other hand, must be borne on a relatively very small number of units.

Further, once a commercial product is developed, the engineering support team continually updates, improves, and bug fixes that product. Again, these costs are distributed over all of the many units that are sold by a large manufacturer. Again, the expenses of such efforts for customized hardware must be borne by a very few units. Often, the number of units makes such levels of support for customized hardware financially unreasonable to offer or to buy. Thus, prior art inspection systems, while perhaps having acceptable speed and accuracy, have been woefully lacking in the categories of flexibility, reliability, and cost.

What is needed, therefore, is a system that overcomes problems such as those described above, at least in part.

SUMMARY

The above and other needs are met by an inspection system for detecting anomalies on a substrate. The inspection system has a sensor array for generating image data. A first high speed network is coupled to the sensor array and receives and communicates the image data. An array of process nodes is coupled to the first high speed network, and receives and processes the image data to produce anomaly reports. Each process node has an interface card coupled to the first high speed network, that receives the image data from the first high speed network and formats the image data according to a high speed interface bus protocol. A high speed interface bus is coupled to the interface card, receives the image data from the interface card. A computer is coupled to the high speed interface bus, and receives the image data from the high speed interface bus and processes the image data according to an algorithm, to produce the anomaly report. A second high speed network is coupled to the process nodes, and receives the anomaly reports from the process nodes. A job manager is coupled to the second high speed network, and receives the anomaly reports from the process nodes and sends information to the process nodes to coordinate the processing of the image data in the array of process nodes.

In this manner, data marshalling can be done ahead of time on a separate machine. Image data processing can be scaled up without a switched fabric. There is no dependence upon any particular type of central processing unit or operating system. Image processing may be accomplished using a graphics processing unit or a field programmable gate array instead of or in combination with a general purpose central processing unit.

In various embodiments, the first high speed network is a fiber optic network, and preferably implements a serial, full duplex data transfer architecture. Preferably, the sensor array includes a time delay and integration sensor. Each process node is preferably a commercially available computer, such as a dual two gigahertz G5 PowerMac computer. Preferably, the high speed interface bus protocol is PCI-X. The second high speed network is preferably a gigabit Ethernet network. Each interface card preferably includes a field programmable gate array that formats the image data for transfer according to the high speed interface bus protocol, a memory that receives and buffers the image data between the interface card and the computer, and four fiber inputs that receive the image data from the first high speed network.

The sensor array preferably provides the image data in four sections, and the first high speed network includes four independent lines, where each of the four independent lines is coupled to a corresponding one of the four sections of the sensor array. The array of process nodes preferably has four columns of process nodes, where each of the four columns of process nodes is coupled to a corresponding one of the four independent lines.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

One advantage of the inspection system 10 described herein is that the components are readily commercially available and do not require customized design and manufacture, except perhaps an interface 22, which is relatively easily produced. This has a number of advantages. First, the reliability of the inspection system 10 is generally increased by using components for which a large engineering effort has been invested, for which upgrades and fixes are continually produced, and which have a good track record in the marketplace. In addition, with large numbers of a single component being produced by the original manufacturer, problems are generally discovered faster and fixed sooner.

Further, commercially available computers, such as the process nodes 20 and other components as described below, can run many different kinds of algorithms, whereas customized hardware, and more especially the customized and optimized hardware that is so prevalent in prior art inspection systems, tends to be extremely limited in what it can do, because the cost of adding additional functionality to such customized hardware is extremely high.

Figure 1:
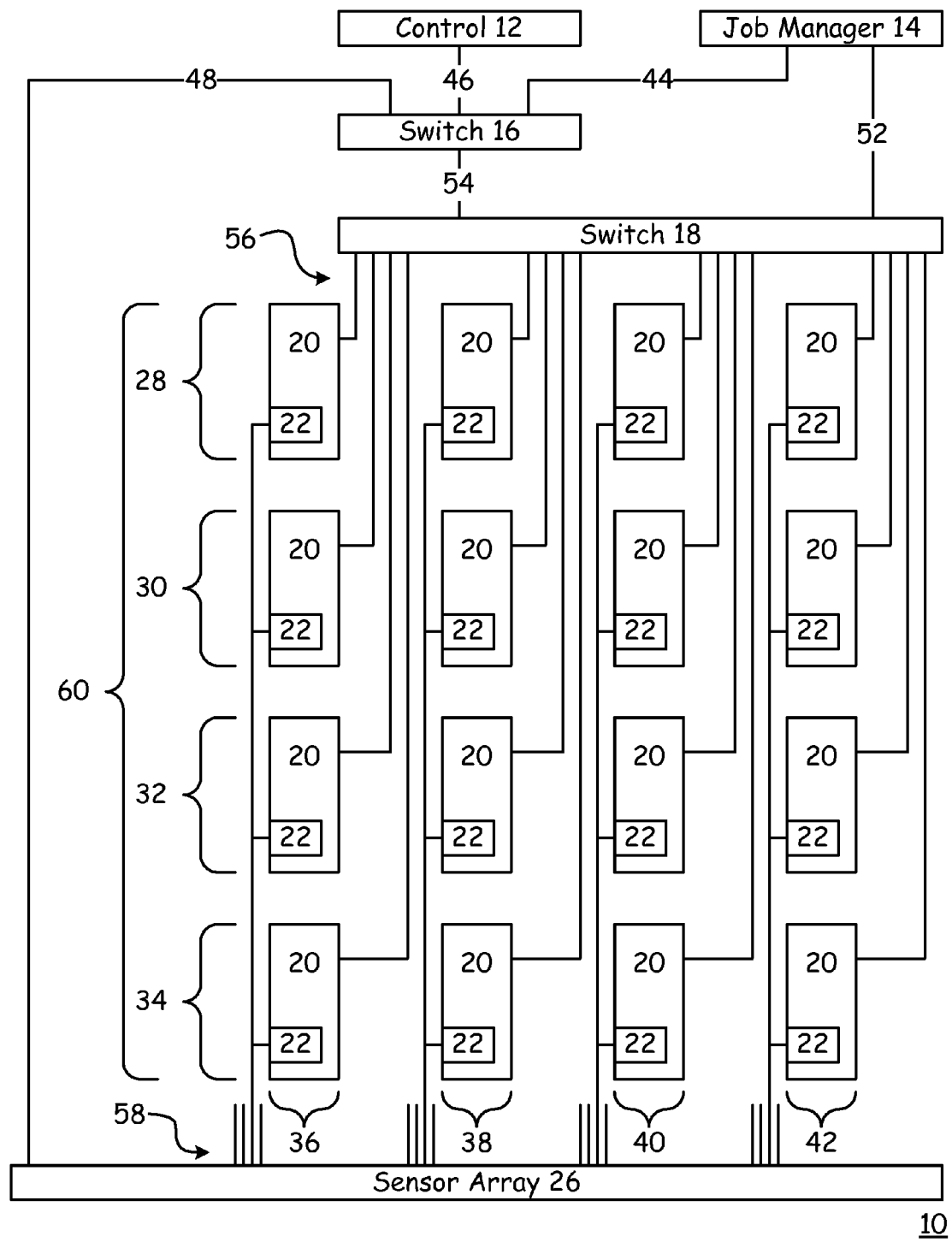
FIG. 1 is a functional block diagram of an inspection system according to a preferred embodiment of the invention.

With reference now to FIG. 1, there is depicted a functional block diagram of an inspection system 10 according to a preferred embodiment of the present invention. A general description of the inspection system 10 is first presented. Following the general description, more detailed descriptions of various aspects of the inspection system 10 are presented.

General Description

The inspection system 10 is preferably used for analyzing image data, such as that gathered from optical sensors. For example, both bright field inspection systems and dark field inspection systems use optical sensors. In various embodiments, the inspection system 10 includes a sensor array 26, which is operable for optically gathering the image data. The sensor array 26 as depicted in simplified form in FIG. 1 preferably includes functions such as those provided by a common run time alignment processor, which sends the image data out on different output streams 58.

The sensor array 26 preferably includes sensors and handling systems for optically inspecting substrates, such as the substrates that are used in integrated circuit fabrication processes, such as semiconductor wafers, masks, reticles, and other such substrates. Thus, the inspection system 10 is particularly well adapted to the integrated circuit fabrication industry, which relies greatly upon the optical inspection of such substrates.

As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

In a most preferred embodiment, the sensors in the sensor array 26 are time domain and integration sensors. However, in other embodiments, other sensor types may also be used. The substrate handling systems in the sensor array 26 are preferably adapted to automatically unload the substrate from an input staging system, such as from a cassette, move the substrate under the sensors, such as by moving one or both of the sensors and the substrate relative to one another, and then load the substrate back into an output staging system, such as a cassette.

Thus, in its most preferred embodiments, the inspection system 10 is adapted to automatically inspect the substrate and produce image data. However, in alternate embodiments the inspection system 10 can accept image data that has been stored for later analysis, either in addition to or in place of image data that is being generated in real time.

Many different factors of the inspection 10 combine to produce a very large quantity of image data at a very fast rate. Because of the very small size of modern integrated circuits, the imaging of the substrates by the inspection system 10 is preferably performed at a very high magnification. The inspection system 10 is preferably adapted to detect anomalies on the substrate, which may be defects such as scratches, extraneous particles, voids, short circuits, open circuits, and so forth. To support the optical inspection of such very small features, the pixel size for the sensors is preferably about one tenth of a micron. This small pixel size is one of the factors in the large amount of image data that is produced, and the high rate at which it is produced.

In addition, the inspection system 10 is preferably adapted to handle relatively large substrates having a diameter of about a foot or more. Further, the substrate handling system of the sensor array 26 preferably moves the substrate as rapidly as can be supported by the rest of the inspection system 10, so that the inspection system 10 can process as many substrates within a given length of time as possible. As introduced above, all of this combines to create a very large amount of image data that is delivered at a very fast rate.

For example, the inspection system 10 preferably generates more than three billion pixels per second, with each pixel having eight grayscale bits. This produces an image data stream of over three gigabytes per second. Thus, the preferred embodiments of the present invention as described in greater detail below are adapted to process large amounts of data through a variety of different means.

The inspection system 10 is preferably under the control of a control computer 12, which provides top level control for the inspection system 10, including the storage, selection, and delivery of the recipes by which the inspection system 10 is controlled, interfacing with system operators, and receipt, storage, and delivery of information from and to other computer systems on a network.

However, because the inspection system 10 preferably handles large amounts of data at high rates as described above, there is preferably at least one job manager 14 that performs most if not all of the detailed control aspects for the various components of the inspection system 10. The number of job managers 14 that are implemented preferably varies according to various criteria, such as the type of inspection that is performed by the inspection system 10—be it bright field or dark field, for example.

The job manager 14 is most preferably a logical structure, such as a set of Java routines that run on a host computer. In a preferred embodiment, the job manager 14 is hosted on a separate computer that is used substantially only for that function. Such a configuration tends to isolate the job managers 14 from other computational demands that may be hosted by a commonly used computer. However, in alternate embodiments the job manager 14 is hosted on a common computing platform, such as on the control computer 12.

The job manager 14 preferably, among other things, directs the transmission of image data to the process nodes 20 for processing. Stated in other words, the job manager 14 does not actually transfer the image data to the process nodes 20, but directs other components of the inspection system 10 to do, as described in more detail below. The job manager 14 preferably also provides instructions for the inspection of the image data to the process nodes 20. The instructions preferably define inspection parameters such as pixel size, optics mode, number of gray scales, inspection swath length, and so forth.

The control computer 12, job manager 14, and sensor array 26 are all preferably in communication with one another through a network, which is most preferably a relatively high speed network such as gigabit Ethernet. It is appreciated that other protocols besides Ethernet could also be used, and speeds other than gigabit could also be used. However, gigabit Ethernet is preferred for this portion of the communication between the components, because it has a relatively high bandwidth that generally supports the design goals of high data throughput in the inspection system 10.

In various embodiments, the network connections 44, 46, and 48 are made through one or more network switches. Alternately, other devices such as routers or hubs could be used for this purpose. In one embodiment, all of these network connections are made through the same switch, such as switch 16 or switch 18. However, in a most preferred embodiment, these network connections are locally made through a first switch 16, so that control information that is delivered between the job manager 14, control computer 12, and sensor array 26 does not steal bandwidth from other network connections, which are described in more detail below.

In such a configuration, the first switch 16 is preferably connected to a second switch 18, such as via a network connection 54. Other network connections are preferably also made to the second switch 18, as described in more detail below. Most preferably, the job manager 14 is connected to both the first switch 16, so as to communicate lower priority instructions to the elements of the inspection system 10 as described above, and also to the second switch 18, so as to communicate higher priority instructions to other elements of the inspection system 10, as describe in more detail below.

The analysis of the image data is preferably accomplished by a node array 60 of the inspection system 10. The node array 60 is preferably an array of process nodes 20, which can be thought of as being disposed in rows 28, 30, 32, and 34 and columns 36, 38, 40, and 42. The number of rows and column as depicted in the node array 60 of FIG. 1 is by way of example only, and is preferably determined by factors that are described in more detail below. The process nodes 20 preferably receive image data on lines 58 of a high speed network, such as a fiber optic network. Although a different protocol may be used for the high speed network 58, such as gigabit Ethernet, Firewire, high speed USB, or fast wide ultra SCSI, fiber optic tends to have greater bandwidth when used in combination with the other components of the inspection system 10 than these other options, and so tends to be more preferred.

The portion of the image data that is delivered on the network 58 to a single column of process nodes 36, 38, 40, or 42 preferably comes from a given portion of the sensors in the sensor array 26. For example, the first column 36 may receive image data from a first quarter portion of a time delay and integration sensor, the second column 38 may receive image data from a second quarter portion of the sensor, the third column 40 from a third quarter portion, and the fourth column 42 from a fourth quarter portion. The process nodes 20 in a given column are preferable connected to the network 58 in a daisy chain topology, as described in more detail hereafter.

In one embodiment, each of the process nodes 20 is a dual processor G5 PowerMac computer running OS X, as manufactured by Apple Computer, Inc. of Cupertino Calif., preferably operating at a clock speed of at least about two gigahertz. The inspection system 10 preferably includes at least twelve of the process nodes 20, which are most preferably disposed in four logical columns of three rows each. However, the same computational capacity might also be provided in other embodiments with a total of eight different three gigahertz, dual processor computers, which are preferably disposed in four columns of two rows each. It is appreciated that the selection, number, and arrangement of the process nodes 20 in the inspection system 10 is adjustable as necessary to handle the desired throughput of image data.

It is appreciated that other computers besides PowerMac computers may be used in the inspection system 10. For example, Opteron based computers, as manufactured by Advanced Micro Devices, Inc. of Sunnyvale Calif., having similar speeds and memory capacity could also be used with the Linux operating system. However, because of the interdependencies of the computations being performed by each of the process nodes 20, most preferably all of the process nodes 20 in a given inspection system 10 are of the same type and configuration. Each of the process nodes 20 preferably includes at least about three gigabytes of memory. The computer hosting the job managers 14 is preferably of a similar class, with some differences. Speed is also important for the job manager 14, but data buffering is less so and storage space is more so than for the process nodes 20. Thus, while the process nodes 20 preferably have lots of memory and no hard drive, the job manager 14 preferably has less memory and at least one hard drive.

The process nodes 20 most preferably receive the image data through an interface 22 that is preferably installed in each process node 20, which interface 22 is adapted to receive the image data on the high speed network 58, and provide it to the process node 20 at a speed that is preferably at least as fast as the speed at which a given process node 20 can process the image data. This speed is most preferably no less than about eight hundred megabits per second. However, in embodiments where a greater number of process nodes 20 can be used, each process node 20 does not need to accept the image data at such a high rate of speed. However, by preferably maximizing the image data delivery rate to the process nodes 20, fewer process nodes 20 are required, and the overall cost of the inspection system 10 is generally reduced. The interface 22 most preferably performs some amount of processing on the image data that it receives, such as verifying checksums, stripping off packet headers, and re-ordering the bits to more fully optimize the image data stream for processing by the process node 20.

The process nodes 20 preferably analyze the image data that is sent to them, and generate reports on the image data that they have analyzed. The reports from the process nodes 20 are preferably delivered to the job manager 14. Most preferably, the process nodes 20 communicate with the job manager, and other elements of the inspection system 10 as may be desired, through the network connections 56. In the preferred embodiment, the network 56 is again a gigabit Ethernet network, and the connections 56 are most preferably made to the second switch 18. However, in other embodiments, other protocols and topologies can also be used, as described above.

The processing of the image data by the process nodes 20 is most preferably accomplished with relatively high speed routines, such as those written in a programming language such as C. Communication between the process nodes 20 and other components, such as the job manager 14, is preferably accomplished with a low overhead routine, such as those written in a programming language such as Java, and most preferably using the remote method invocation protocol.

Because the process nodes 20 receive image data at an extremely high rate, they tend to generate the reports at a high rate. However, because the reports preferably do not contain as much data as the image data, a relatively slower network can be used to communicate the reports to the job manager 14 than is used to communicate the image data to the process nodes 20. Therefore, high speed fiber 58 is preferably used for the image data, and relatively slower gigabit Ethernet 56 is preferably used for reporting. It is appreciated that the network 56 may run at a slower speed than gigabit, such as one or more of the automatic fallback rates of one hundred megabits per second and ten megabits per second, as supported by the gigabit Ethernet protocol.

Preferably, the network 56 also carries instructions from the job manager 14 to the process nodes 20. These instructions include information such as set up data and processing instructions that are to be performed on the image data. Because the process nodes 20 are operating under a relatively heavy computational load, and thus may require such instructions at a fairly rapid rate, and also because the reports delivered by the process nodes 20 are sent at a relatively high rate, the job manager 14 preferably has a second network connection 52 to the second switch 18, through which such higher priority communication is preferably accomplished.

Various aspects of the inspection system 10 are now presented in greater detail in the following sections.

Image Data Interface

As introduced above, the image data delivered to the process nodes 20 is most preferably divided into four streams, with each stream preferably representing a one-quarter portion of an inspection swath on the substrate that is about five hundred and twelve pixels wide. One of each of these four image data streams is preferably delivered to one of each of the four columns 36, 38, 40, and 42 of the process nodes 20. As mentioned above, the number of columns and the segmentation of the image data stream can be set at other values besides four. The fiber optic network 58 preferably delivers the image data at a rate of about eight hundred megabytes per second. In a preferred embodiment, the fiber network 58 implements a serial, full duplex data transfer architecture.

Figure 2:
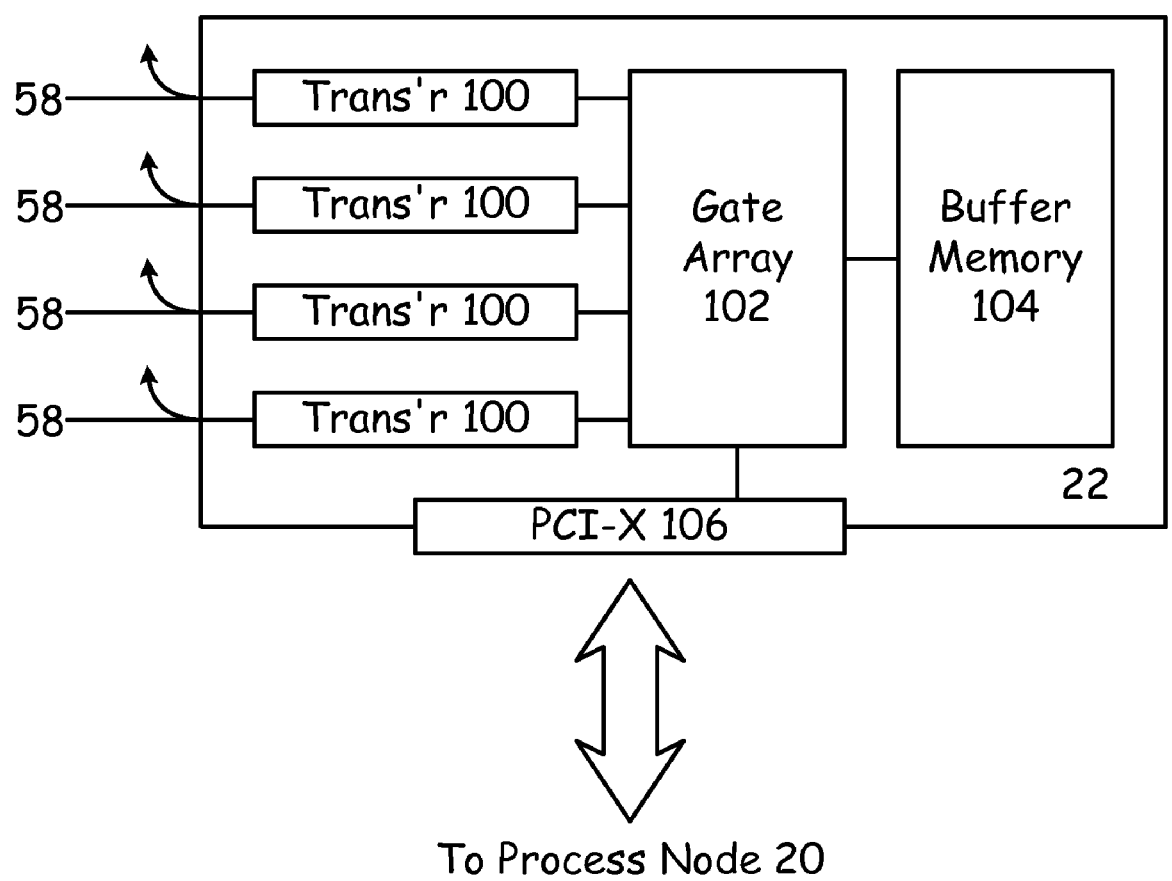
FIG. 2 is a functional block diagram of an interface of a process node of the inspection system of FIG. 1, according to a preferred embodiment of the invention.

In the embodiment of FIG. 1, the image data is received by the interface 22, which is preferably installed in each process node 20. In one preferred embodiment, the interfaces 22 are input data adapter cards having serial fiber optic inputs, such as transceivers 100, which convert the fiber optic image data received on the fiber network 58 into electrical image data, and deliver the image data to a pre processor, such as a field programmable gate array 102, all as depicted in FIG. 2. The transceivers 100 preferably support a bandwidth of about two and a half gigabits per second. Most preferably, each of the interfaces 22 has four such transceivers 100, with each of the transceivers 100 in each process node 20 of a given column 36, 38, 40, and 42 independently daisy chained to the corresponding transceivers 100 in each of the other process nodes 20 within the column 36, 38, 40, or 42 of the node array 60. Thus, the network 58 preferably provide four connections to each column of process nodes 20 in the node array 60. Three of these four connections are depicted as stubs in FIG. 1, so as to not unduly burden the figure with detail.

In some embodiments, the gate array 102 provides some image data processing functions, such as segmented auto thresholding histogramming. The gate array 102 is preferably additionally adapted to handle input tracking, input processing, PCI-X interface, and memory interface processes. The interface 22 preferably includes at least about one to two gigabytes of buffer memory 104, which is used to buffer the image data as necessary prior to transferring it to the memory in the process node 22. If the process node 20 can keep up with the flow of image data received on the network 58, then no buffering is needed. However, if the process node 20 cannot sustain that rate of data flow, such as for intermittent periods of time, then the backlog of image data is preferably buffered in the memory 104. The interface 22 preferably communicates with the process node 20 through a PCI-X slot 106, although interface protocols with similar bandwidth capabilities of at least about eight hundred megabits per second could also be used.

Memory Load Balancing

As described above, the process nodes 20 are preferably adapted to store a portion of the image data that they receive, such as within the buffer 104 of the interface 22. Thus, the process nodes 20 preferably have a sufficient amount of memory to continue receiving image data even if the rate of analysis of the image data within the process node 20 falls below the rate of data acquisition by the process node 20. In this manner, the inspection system 10 can readily handle a peak load of image data without slowing down image data acquisition and analysis.

For example, at a standard load of delivery of the image data, a given process node 20 may be able to process the image data at a faster rater than it is delivered. In such a situation, the buffer memory 104 is generally not used to buffer any significant amount of the image data, because there is no need to relieve the computational load on the process node 20. However, for various reasons, such as the scanning of particularly complex portion of the substrate that is being inspected, a relatively large amount of image data may be delivered within a brief period of time, or the process node 20 may take a longer period of time to process the image data that it has already received.

If the additional image data load extends beyond that which the process node 20 is capable of processing on the fly, the additional image data load is preferably buffered, such as in the memory 104 in a first in, first out process. Then, when the image data load ebbs again, the process node 20 receives the buffered image data, and starts receiving the image data without it building up a load within the buffer 104. Such control of the delivery of the image data is most preferably under the control of the gate array 102, as explained in more detail elsewhere herein.

With the buffer 104 configuration as described above, the software requirement for the inspection system 10 is significantly less than that for prior art inspection systems. For example, the job manager 14 preferably does not provide dynamic load balancing between the process nodes 20, because the process nodes 20 are preferably assigned to a segmented stream of the image data from the sensor array 26, and have sufficient memory and speed for handling the peak loads of the image data stream. Thus, no complex and expensive switched fabric topology is needed, as is commonly employed in prior art systems. Further, the number of process nodes 20 used in the node array 60 can be kept at a number that is less than that which would otherwise be required to handle a peak load of image data, resulting in a lower overall cost for the inspection system 10, without compromising the throughput of the inspection system 10.

Status Polling

As introduced above, the image data is preferably moved from the interface 22 to the process node 20 via direct memory access. As the process node 20 is able to accommodate more image data, the interface 22 delivers the image data through the PCI-X interface 106, and when the process node 20 cannot handle more image data, the interface 22 buffers the image data in the buffer memory 104.

In prior art designs, an interrupt is used as a signal when more data can be delivered via a direct memory access process. However, interrupts are typically handled by the central processing unit of the host, which in this case is the process node 20. As described at length above, the process node 20 is under a severe computational load, and various aspects of the inspection system 10 are designed to preferably keep the process node 20 processing image data as fast as it can. Thus, any additional computation load on the process node 20 is unwelcome.

Therefore, the inspection system 10 according to the preferred embodiments of the invention does not use interrupts to signal when additional image data can be delivered via direct memory access to the process node 20. Rather, a polling method is used. In one embodiment, the gate array 102 polls a register or some other memory location to determine the status of the register. When the register is in a first status, then the process node 20 will accept more image data via direct memory access, and when the register is in a second status, then the process node 20 will not accept more image data via direct memory access. In this manner, the image data is delivered in a smooth manner via direct memory access, without losing the processing cycles on the process node 20 that would otherwise be required to handle an interrupt.

Daisy Chain Topology

The benefits of disposing the process nodes 20 into columns 36, 38, 40, and 42 have been generally described above. Some of the benefits of disposing the process nodes 20 into different rows 34, 32, 30, and 28 are now described. In addition to load leveling the computational demands of the inspection system 10 by increasing the memory capacity of the process nodes 20 and providing buffer memory 104 in the interface 22, the architecture of the node array 60 also both increases the capacity and levels the computational load of the inspection system 10.

For example, with reference to FIG. 1, first swaths or portions of the image data stream are sent out on the network 58. Because the four process nodes 20 in row 34 of the node array 60 are not working on anything else at the time that the first portion of the image data is delivered, they accept the first portion of the image data, and the process nodes 20 in row 34 begin processing the first portions of the image data. While the process nodes 20 in row 34 are still processing the first portions of the image data, second portions of the image data stream are sent out on the network 58. However, this time the four process nodes 20 in row 34 of the node array 60 are busy processing the first portion of the image data stream, and thus they preferably do not accept the second portion of the data stream.

Instead, the transceivers 100 of the interfaces 22 reflect the second portions of the image data stream back out onto the network 58, to be received by the four process nodes 20 in row 32 of the node array 60. Because the four process nodes 20 in row 32 of the node array 60 are not doing anything else at the time, they accept the second portions of the image data, and the process nodes 20 in row 32 begin processing the second portions of the image data. By the time third portions of the image data stream are provided by the sensor array 26 on the network 58, and one or more of various different options can be implemented.

In a first example, the process nodes 20 in row 34 of the node array 60 have completed processing the first portions of the image data stream, and thus they can receive and process the third portions of the image data stream. If the process nodes 20 in row 34 of the node array 60 have not as yet completed processing the first portions of the image data stream, then the third portions of the image data stream can optionally still be sent to the process nodes 20 in row 34, to be buffered in memory, such as the memory 104, before being processed by the process nodes 20, because each of the process nodes 20 preferably has enough memory to hold at least two such portions of image data. In this manner, as long as no one of the process nodes 20 within a row of the node array 60 does not get too far behind in computation, the inspection system 10 will not stall.

Alternately, additional rows 30 and 28 of process nodes 20 may be implemented in the node array 60. In this manner, either the memory requirements for each of the process nodes 20 may be reduced, or the speed at which image data is delivered to the inspection system 10 may be increased, or additional processing of each portion of the image data may be accomplished by each process node 20. In one embodiment, the control of such decisions is preferably specified at the job manager 14, and implemented within the gate array 102, which determines whether it will or will not accept the image data.

This bumping of the successive portions of the image data is enabled, at least in part, by the daisy chain topology of the network 58. Preferably under the control of the gate array 102, portions of the image data are bumped to rows of process nodes 20 that are deeper within the node 60, when the shallower process nodes 20 are busy. In a most preferred embodiment, if one of the process nodes 20 within a row of the node array 60 is not able to accept an image data portion, then none of the process nodes 20 within the row of the node array 60 accepts the image data portion, and the image data portion is bumped via the network 58 to the next deeper row of process nodes 20 within the node array 60. In alternate embodiments, the different columns of process nodes 20 within a given row are more independent, and bumping occurs within a given column from one row to another based only upon the load of the shallower process nodes 20 within that column.

In alternate embodiments, this daisy chain topology as preferably implemented in the fiber network 58 can be implemented in other network protocols, such as gigabit Ethernet. However, fiber network 58 is preferred because of the generally greater bandwidth which it affords.

The number of rows and columns in the node array 60 and the processing capabilities of the process nodes 20 are all preferably interrelated. It is preferred to send image data to the node array 60 on the network 58 as fast as it can be generated by the sensor array 26. Thus, it is also preferred to process the image data with the node array 60 as fast as it can be sent by the network 58. By increasing the number of column within the node array 60 and dividing the swath of image data into a number of different segments that preferably corresponds to that number of columns, the computational requirements of each process node 20 in the node array 60 generally decreases for a given level of image data delivery. By increasing the number of rows within the node array 60, the computational requirements of each process node 20 in the node array 60 further generally decreases for a given level of image data delivery.

By selecting process nodes 20 with as high a computational capacity as is practical, the number of rows and columns in the node array 60 can generally be reduced for a given level of image data delivery. Thus, process nodes 60 with relatively high computational capacities are preferably selected. The number of rows and columns in the node array 60 is then preferably set so that the node array 60 can process an amount of image data that represents the faster average amount that can be delivered by the sensor array 26 on the network 58. Memory is added to either the process node 20 or the interface 22 as described above to handle any additional, intermittent computational load that might be required, as described above. In this manner, the inspection system 10 does not specify either too few or too many process nodes 20.

Full Swath Analysis

In the embodiments described above, the image data for a single swath has preferably been segmented as delivered from the sensor array 26, such as into four quarter portions. It is appreciated that other segmentations could also be used. However, in some embodiments, no segmentation of the image data is desirable. Such an embodiment would, for example, allow for a greater portion of the imaged substrate to be used for detection of anomalies, such as defects. Such segmentation can be specified, for example, by the job manager 14, and implemented in one or more of the various components that are generally referred to as the sensor array 26 herein.

As described elsewhere above, the process nodes 20 preferably contain sufficient memory, either within themselves or within the buffer memory 104, to enable continued acquisition of image data even if the rate of analysis of the image data in the process node 20 falls behind the rate of image data acquisition. The process nodes 20 may also contain sufficient memory so that an entire swath width of the image data may be sent to a single column 36, 38, 40, or 42 of process nodes 20, without segmenting the image data.

The architecture of the inspection system 10 would not need to change from that as depicted in FIG. 1. Rather, the job manager 14 could instruct the appropriate elements of the sensor array 26 to provide the entire swath of the image data along a single output of network 58 to a single column of the node array 60. Alternately, the architecture of the node array 60 could be changed to a single column. However, accomplishing the image data delivery as described in this section by using instructions to the sensor array 26 rather than altering the architecture of the node array 60 provides for a much more adaptable inspection system 10.

To implement such an embodiment, each process node 20 would preferably have about six gigabytes of memory, which could either be resident in the process node 20 itself, or within the buffer memory 104.

Mirror Node Verification

One goal of inspection system 10 is to maintain consistent and uniform processing by each of the process nodes 20. Each process node 20 in the node array 60 preferably produces a report that is substantially similar to the report that would be generated by any other process node 20 in the node array 60. Ensuring that this condition is met is of particular concern when new hardware or software is introduced into the inspection system 10.

In the preferred embodiment, a new process node 20 is configured to mirror one of the existing process nodes 20 within the node array 60. The job manager 14 is preferably configured to send instructions to both the existing process node 20 and the mirror node. Most preferably, the instructions are redundant in the case of the mirror node, so that the results from the mirror node can be compared to the results from the existing process node 20. The mirror node is preferably programmed by the job manager 14 to produce the output that the process node 20 produces, including information such as defect results, images, histograms, and projections.

The mirror node can exist in various logical positions within the inspection system 10. for example, the mirror node may be disposed within the node array 60, such as on one of the deeper rows 28 or 30, so that it resides within a row that can be turned off in regard to normal image data processing, without substantially effecting the throughput of the inspection system 10. Alternately, the mirror node can be on the network 56, such as through the switch 18, but be logically outside of the node array 60, in that it does not reduce the computational ability of the node array 60 in any manner.

In yet another embodiment, the mirror node can be placed anywhere within the node array 60, but the job manager 14 instructs the inspection system 10 to always have the process node 20 that is one row deeper within the same column of the node array 60 to also process the image data that is received by the mirror node. This is accomplished such as by the interface 22 reflecting all of the image data that is received by the mirror node back out along the network 58 to be received by the next deeper process node 20, which is connected to the network 58 in the daisy chain topology, as described in more detail elsewhere herein.

The job manager 14 preferably verifies whether the mirror node and the process node 20 produce results that are in agreement within an allowable tolerance. If they are not, then there is a problem with one or more of the mirror node and the process node 20, and the job manager 14 reports this condition. The job manager 14 is preferably programmed to not reject an inspected substrate based upon either a bad report from the mirror node or a discrepancy between the mirror node and the process node 20.

If a discrepancy of too great a size exists between the mirror node and the process node 20, it may be an indication that the mirror node is unacceptable, or alternately, it may be an indication that the process node 20 is faltering. In this manner, the mirror node can be used as a check of the various process nodes 20 within the node array 60. Further yet, a discrepancy may be an indication that both the mirror node and the process node 20 are faulty.

In some embodiments, the mirror node is a candidate computer that is of unknown performance, and the purpose of connecting the mirror node to the inspection system 10 is to determine whether the mirror node is acceptable. In alternate embodiments the mirror node is known to be acceptable, and the purpose of connecting the mirror node to the inspection system 10 is to verify that the process node 20, which may be of unknown performance, is equivalent to the mirror node. In these embodiments the mirror node is a known good computer.

If the mirror node is a candidate computer and the report from the mirror node is unacceptably different from the report provided by the process node 20, then the mirror node is judged to not be acceptable. If the mirror node is a known good computer and the report from the mirror node is unacceptably different from the report provided by the process node 20, then that process node is judged to not be acceptable, and the job manager 14 preferably identifies it as a failed process node 20. Under such circumstances, the reports from the mirror node may be substituted for the reports from the failed process node 20, until the failed process node 20 can be replaced.

In some embodiments, the job manager 14 cyclically transmits the common portion of the image data to the mirror node and the process node 20 for which the reports are being compared. In some embodiments involving cyclical transmission, a regression analysis is performed on the test results to determine differences among some or all of the process nodes 20, and between the process node 20 and the mirror node.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An image processing system comprising:

a sensor array adapted to generate image data, a fiber optic network to communicate the image data from the sensor array to an interface card, the interface card adapted to receive and format the image data for transfer according to a high speed interface bus protocol, an image processing device having a high speed interface port, a job manager for providing instructions to the image processing device in regard to processing of the image data, the job manager connected to the image processing device on a high speed network that is separate from the fiber optic network, and a high speed interface bus coupled to the interface card and the high speed interface port, and adapted to transfer the formatted image data to the image processing device through the high speed interface port according to the high speed interface bus protocol.

* * * * *